United States Patent [19]
Schwarz

[11] 3,967,621
[45] July 6, 1976

[54] NEEDLE HOLDER FOR MEDICAL SYRINGES, VIALS, OR THE LIKE

[76] Inventor: Lothar Schwarz, Belchenstrasse 1, 75 Karlsruhe 51, Germany

[22] Filed: July 14, 1975

[21] Appl. No.: 595,634

[30] Foreign Application Priority Data

July 16, 1974 Germany.............................. 2434046

[52] U.S. Cl................................. 128/216; 128/221
[51] Int. Cl.[2]......................................... A61M 5/00
[58] Field of Search................ 128/215, 216, 218 R, 128/218 N, 218 M, 220, 221, 272; 206/364, 365, 366

[56] References Cited
UNITED STATES PATENTS

| | | | |
|---|---|---|---|
| 2,400,722 | 5/1946 | Swan | 128/215 X |
| 3,052,241 | 9/1962 | Myerson et al. | 128/221 |
| 3,171,412 | 3/1965 | Braun | 128/272 |
| 3,367,331 | 2/1968 | Brookfield | 128/221 |
| 3,401,693 | 9/1968 | Cohen | 128/221 |

Primary Examiner—John D. Yasko
Attorney, Agent, or Firm—Andrus, Sceales, Starke & Sawall

[57] ABSTRACT

A needle holder includes a base body which receives the puncturable closure of a medical preparation holder. A hub part, containing the needle, is mounted in the base body through a first threaded connection for movement to a work position in which the needle punctures the closure. A protective sleeve for the needle is mounted on the base body through a second threaded connection, oppositely threaded with respect to the first connection. The sleeve and the hub part are coupled by an axial gear tooth arrangement which permits axial movement of the hub part upon rotation of the protective sleeve on the base body.

The base body may exhibit a variety of forms, the second threaded connection may include a saw tooth profile which permits the protective sleeve to be slid on a base body without rotation, and a friction coupling may be provided between the hub part and the protective sleeve.

15 Claims, 8 Drawing Figures

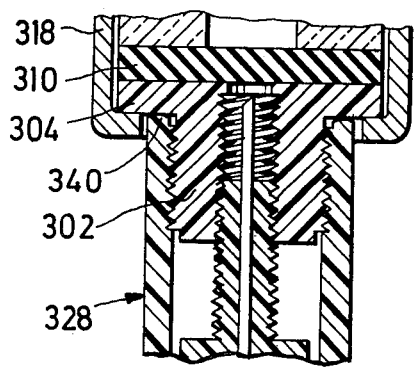
FIG.3
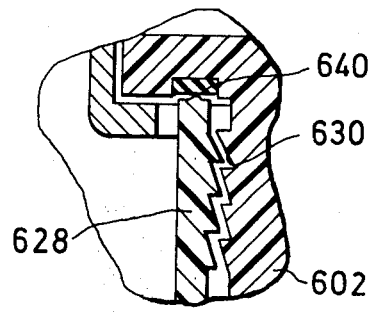
FIG.6
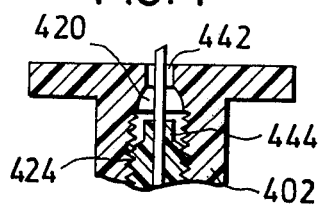
FIG.4
FIG.7
FIG.5
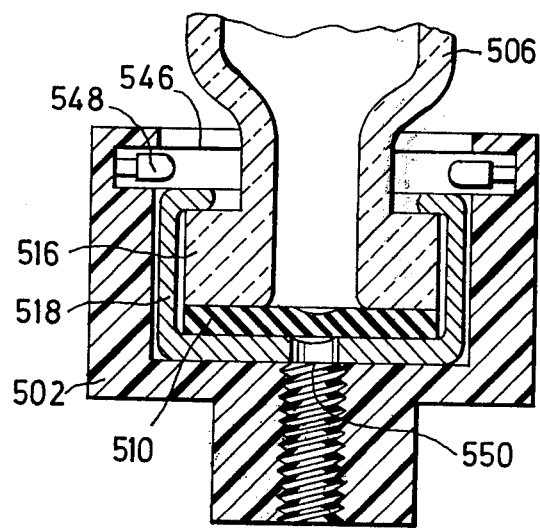
FIG.8
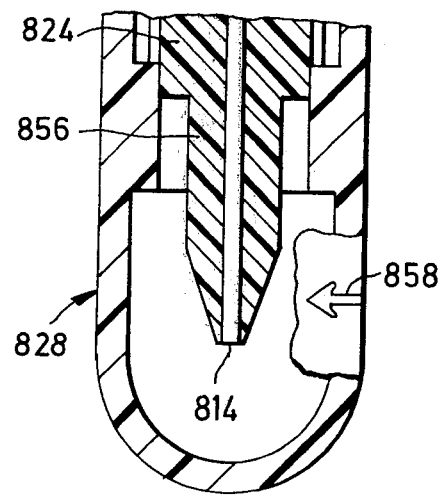

NEEDLE HOLDER FOR MEDICAL SYRINGES, VIALS, OR THE LIKE

BACKGROUND OF THE INVENTION

1. Field of the Invention

The present invention relates to a needle holder for medical syringes, such as injection syringes and syringes for the removal of body fluids and for, vials such as eyedrop vials, and the like.

2. Description of the Prior Art

With medical syringes, in particular injection syringes, the holder for the hollow needle or cannula is so formed that it is with difficulty that the needle and associated preparation holder can be connected together in a sturdy unit in a simple manner while avoiding the danger of infection. In many cases, the needle together with a base body to which it is connected and a protective sleeve which surrounds the free end of the needle are kept sterile in a sealed packaging. After the removel from the packaging, the base body is mounted on a sterile end of the preparation holder which is provided with a puncturable closure, whereby the end of the hollow needle from the protective sleeve punctures the closure. The preparation holder with the so engaged needle is inserted in a syringe body, which is ordinarily formed out of metal and to the entire arrangement imparts the necessary strength to the application. This mode of operation is not only complicated but also brings the danger of infection with it since the puncturable closure of the preparation holder and the therewith connected end of the needle must be exposed before their joinder and under these conditions can become contaminated. Another disadvantage is the requirement that an additional syringe body be used which is not only inconvenient but is also productive of additional danger of infection.

There are therefore known ampule syringes in which the preparation holder serves simultaneously as the syringe body. Such syringes are ordinarily suitable for a single use and the simple and inexpensive construction required for such service makes it naturally difficult to form the needle holder with sufficient strength and load capacity. A known solution suggested in this regard exists in which with ampule syringes, the needle is mounted on the preparation holer (ampule or syringe body). A sealing arrangement must naturally be provided which hinders the flow of the preparation out of the needle until immediately before the operation of the gasket arrangement is made ineffective. As the gasket arrangement employs, for example, the protective sleeve, this then on its closed end is provided interiorly with a sealing material, for example a rubber stopper which closes the outer end of the needle until removal of the protective sleeve. The permanent contact of the preparation with the metal needle produced by this ampule construction is however, most undesired. It is therefore further known for the sealing device to provide additionally a puncturable closure on the preparation holder and an arrangement so to form that by retention of the covering effected by the protective sleeve against surrounding action a relative movement between the closure and the needle can be defined through which the needle punctures the closure. The closure and/or the needle can thus be moved. It is difficult to produce a needle holder which renders such relative motion with the necessary reliability and convenient service and which needle holder is also sufficiently simple to be suitable for use with a single use syringe.

SUMMARY OF THE PRESENT INVENTION

The invention overcomes these difficulties and provides a needle holder which by a simple construction secures a strong anchoring of the needle on the preparation holder and by the assembly with the preparation holder, connects the needle in a simple and reliable way to the inside of the preparation holder while maintaining the closure against outside action.

To the solution of this problem the invention departs from known needle holders for medical syringes, vials, and the like by providing a base body for the mounting of a closure of a preparation holder puncturable by a hollow needle. A hub part fastened to the hollow needle is threaded by means of a screw coupling with the base body into a work position in which the end of the hollow needle has punctured the closure of the preparation holder. A protective sleeve is detachably mounted and rotated with an open end on the base body by means of encirclement of the hub and the thereon supported hollow needle. Between the hub part and the protective sleeve is provided a relative axial movement between a beginning screw position and the work position by an axial gear tooth system which couples the hub part to commonly turn with the protective sleeve mounted on the base body.

In accordance with the invention, a second screw connection is provided between the base body and the protective sleeve which is oppositely threaded with respect to the first screw connection. With the untwisting of the protective sleeve from the base body, the fixed hub part, which is by the axial gear tooth system drivingly connected with the protective sleeve is threaded into the work position.

With the last described known needle holder it is provided that the hub part with the thereon mounted needle is threaded in the base body by rotation of the protective sleeve and thereby the needle punctures the closure. The protective sleeve is however simply revolvingly mounted on the base body and can indeed without previous rotation be pulled off so that the desired mode of operation is not secured without additional means. To prevent the danger that through rotation in the wrong direction of the hub part and the needle they become unthreaded from the base body a ratchet and pawl is provided with known needle holders between the protective sleeve and the base body which is employed in the manufacture and allows other disadvantages to exist in that the protective sleeve simply without rotation or according to only insufficient rotation is drawn off.

With the needle holder of the invention false handling is not possible. The protective sleeve cannot be drawn off without rotation. The protective sleeve is threaded on the base body so that it secures an unobjectionable sealing closure to the outside. The unthreading results automatically from the the correct rotation direction without requiring a ratchet and pawl. Even if through partial unthreading, the protective sleeve is through error further threaded on, no additional action can result other than the restoration of the original condition. In no way thereby can the hub part become unscrewed and the threaded engagement between the hub part and the base body be lost so that the device become unusable. The needle holder of the present invention is also simple ad economical in manufacture in that the pitch of the threads necessary for the second threaded connection can be simply with the manufacture of the part in a work station molded.

It will be understood that the second threaded connection may be so dimensioned that with the unthreading of the protective sleeve the latter becomes disengaged not later than when the hub part is threaded into contact with the base body. Preferably the second threaded connection is so dimensioned that with the unthreading of the protective sleeve the latter becomes engaged shortly before the attainment of the working position of the hub. Thus the user will, in each case, further rotate about this position so that, the attainment of the work position of the hub part is assured. For this mode of operation it is further appropriate to so dimension the axial tooth gear system that the rotation driving connection between the protective sleeve and the hub part is initially lost after fully unthreading and a further axial parting movement of the protective sleeve.

The needle holder of the present invention can with advantage be so employed that it is initially assembled so that the hub part is entirely threaded in its work position and then the protective sleeve attached and threaded on whereby the hub part is returned out of its work position to an initial threaded position. The needle holder can then as a unit be sterile packed and preserved for later use. By this manner of use the base body is preferably so formed that it is attachable on the preparation holder. Instead of this, the needle holder according to the invention can, according to the described steps of assembly, connect with a preparation holder and the needle holder and preparation holder together sterile packed. This is particularly advantageous for a single use syringe.

Another possible assembly form is available, in that in a further embodiment of the invention the second threaded connection is provided with thread profiles which axially slide upon one another by the application of increased axial force. With this embodiment it is possible to connect the base body separately with the preparation holder, then to thread the hub part into an initial threaded position with the base body and finally to mount the protective sleeve axially on its threads on the base body. In this embodiment of the invention it is particularly advantageous to use thread profiles in the second threaded connection which in the movement direction corresponding to screw tightening are slidable upon one another and in the movement direction of the protective sleeve corresponding to unscrewing engage one another. In this manner the above described assembly provides simplified attachment of the protective sleeve while at the same time preventing with certainty that through use of excessive force, the protective sleeve could be drawn off without rotation being effected.

Another possibility for a simplified assembly also according to the already present connection between the base body with the preparation holder is presented in another embodiment of the invention in which an elastically flexible friction coupling is provided between the hub part and the protective sleeve in the axial movement direction. The coupling can be formed in a particularly simple way out of at least one tightly seated ring of an elastically flexible material, for example, plastic. With the use of such an axial flexible friction coupling assembly can be obtained by pushing the hub part and the associated needle in the open end of the protective sleeve. The hub part remains, as a result of the operation of the friction coupling, in the initial place and position. The protective sleeve is then threaded on the base body. The thereby accomplished rotational movement corresponds to the unthreading direction of the hub part in the base body so the hub part cannot with the base body connect. With the progressive threading of the protective sleeve on the base body the hub part is drawn from the base body further in the protective sleeve; however through the axial spring action of the friction coupling at all times the structure is biased towards the base body and thereby help in position. In the base body with the rotation of the protective sleeve in the opposite direction, as by the unthreading of the protective sleeve, immediately the first threaded connection provided between the hub part and the base body steps into engagement and then the hub part in the desired manner is threaded in the base body to the work position.

In another form of the invention an effective seal is provided between the protective sleeve and the base body by the tightening threading of the protective sleeve. The forcible entry of contaminants in the protective sleeve is thus prevented with certainty. This affords particularly with an assembly connected with a preparation holder the special advantage that a further repacking for sterile storage can be omitted.

In many cases, the second threaded connection provided for the threading of the protective sleeve is desired to occupy a smaller axial space than corresponds to the threaded and puncturing movement of the hub part and the associated needle. In this case it is preferable for the two threaded connections to have different thread pitches. The second connection may have a smaller thread pitch than the first connection.

The advantages of the needle holder of the present invention are especially apparent as a single use syringe, with which the needle holder is mounted on the preparation holder or the syringe body.

The use of the needle holder is very simple, certain and easy, the needle is without contact driven through the closure and anchored, and the entire device is very simple and with small expenditure manufactured in plastic mass production.

BRIEF DESCRIPTION OF THE DRAWING

The invention is described in the following with the aid of exemplary embodiments in connection with the drawings from which all of the characteristics differentiating the invention from the prior art can be seen.

In the Figures:

FIG. 3 is a partial view similar to FIGS. 1 and 2 showing, in part, another connection between the preparation holder and the needle holder;

FIG. 4 is a view similar to FIGS. 1 through 3 showing in detail a changed exemplary embodiment;

FIG. 5 is a view resembling FIGS. 1 through 4 showing another form of the connection between the preparation holder and the needle holder;

FIG. 6 is a view according to FIGS. 1 and 2 showing an enlarged partially cut away representation, particularly of the second threaded connection;

FIG. 7 is a view according to FIGS. 1 and 2 of a partial showing of an embodiment with a friction coupling; and FIG. 8 is a view according to FIGS. 1 and 2 of a partial showing of an embodiment for a drop vial.

DESCRIPTION OF THE PREFERRED EMBODIMENT

Figure 1:
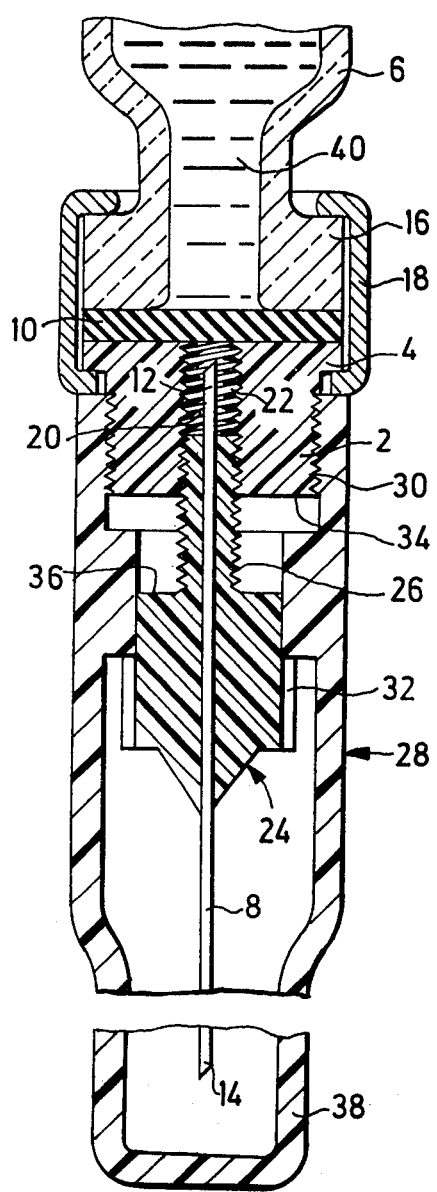
FIG. 1 is a not to scale schematic longitudinal section view through a needle holder according to the invention with the associated preparation holder in the storage condition.
Figure 2:
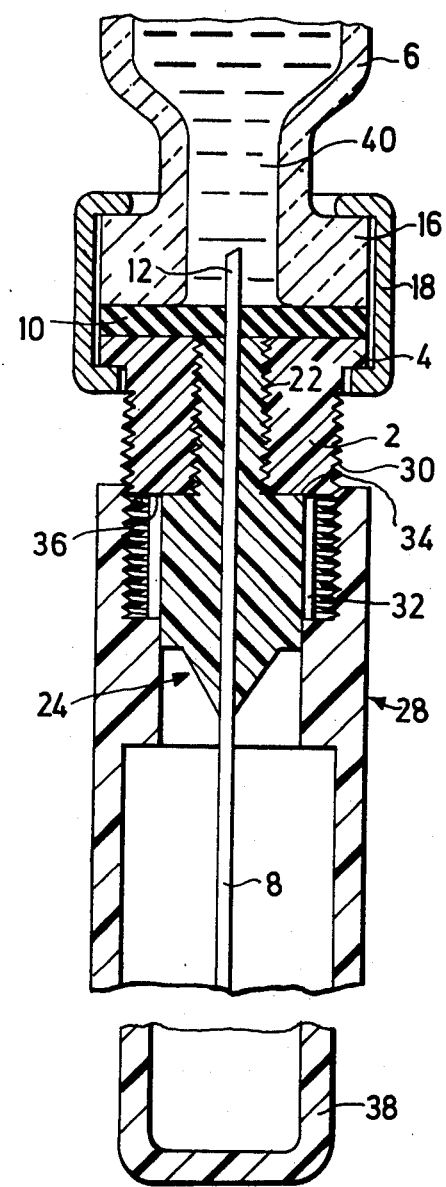
FIG. 2 is a view corresponding to FIG. 1 with the hub part located in the work position.

The needle holder shown in FIGS. 1 and 2 contains a base body 2, which for example may be formed of an appropriately soft, chemical inert material such as polyethylene. This base body has a flange 4 and serves as a closure in the end of preparation holder 6 which presents closure 10 which may be punctured by hollow needle 8. The closure 10 may be formed in the usual manner out of rubber or rubber like material which is inert with respect to the preparation in preparation holder 6. The hollow needle is sharpened in the customary manner on the end 12 adjacent closure 10. If the syringe is an injection syringe or a syringe for the removal of body fluids the other end of the needle 14 is also sharpened in a known manner. The preparation holder 6 has a flange 16 and the two flanges 4 and 16 are connected with each other with the imposition of closure 10 with the help of a cuff 18 which may be formed out of metal and serves to securely couple the flanges together.

In the base body 2 is located a central passage 20 which is provided with threads 22. In the disclosed exemplary embodiment threads 22 extend from the lower end as shown in the Figures to a position short of the upper end of the passage 20 as shown in the Figures.

The closure 10 can also only in passage 20 be provided, then can a separate seal between the base body 2 and the flange 16 be provided or these parts embodied in a piece as is appropriate in a syringe formed completely out of plastic.

A hub part 24 has an outer thread 26 suitable for thread 22 and is by means of the threaded connection formed out of the threads 22 and 26 threaded in the base body 2 and is so moved to the work position shown in FIG. 2 in which the end 12 of hollow needle 8 has punctured closure 10 of preparation holder 6. In FIG. 1 the hub body 24 is shown in a beginning twist position in which the end of the hollow needle 8 is spaced a distance from the closure 10.

The hub part 24 and the therein formed hub 11 are surrounded by a protective sleeve 28 which has an open end and a closed end and with its open end is unthreadable off the base body with the help of a second screw connection. In the embodiment shown it is assumed that the pitch of the threads of both screw connections 22–26 and 30 are similar. The direction of the threads of both screw connection is however opposite.

Between the hub part 24 and the protective sleeve 28 is an axial gear tooth system provided which a relative axial movement permits and which within its zone of contact produces a rotating drive connection between the protective sleeve and the hub part 24. This axial zone corresponds at least to the region between the initial position of the hub part 24 shown in FIG. 1 in the base body 2 and the work position shown in FIG. 2. The work position is characterized in that the needle has punctured the closure 10 whereby it is meaningless how far the needle enters the preparation holder. For a stronger seating of the needle can it advantageously be that the work position is defined through a mating. With the disclosed embodiment is the seating through a shoulder 34 on the hub body 24 effected which abuts with the under surface 36 of the base body 2.

It will be apparent by a comparison of FIGS. 1 and 2 that as a result of the opposite thread direction of screw connections 22–26 and 30 with the untwisting of protective sleeve 28 from the base body 2, the fixed hub part 24 which is by the axial gear tooth system drivingly connected with the protective sleeve 28 is threaded into the working position. The required opposing dependency of the axial position of the hub 24 and the protective sleeve 28 with regard to the base body 2 must naturally be considered in the assembly.

As may be seen from FIG. 2 it is possible to so dimension the second screw connection that with the untwisting of the protective sleeve 28, the connection steps out of engagement approximately with the attainment of the work position of the hub part 24 shown in FIG. 2. With the disclosed embodiment the second screw connection, what is more, so dimensioned that the screw connection with the untwisting of protective sleeve 28 arrives out of engagement just short of attainment of the working position of hub part 24. It is thereby precluded that hub part 24 through seating 34, 36 achieves the end position as a result of manufacturing errors or errors in the assembly of hub part 24, so that hub part 24 thus cannot be further driven before protective sleeve 28 is entirely unthreaded from the base body 2. It will be appreciated, on the other hand, that with the dislcosed embodiment, the axial gear tooth system is so dimensioned that the rotating driving connection between the protective sleeve and the hub part is at first lost after fully unthreading and a further axial parting movement of the protective sleeve. It is thus apparent that also after the loosening of the second connection 30 the hub part 24 is fully threaded in the work position shown in FIG. 2.

In the use of the disclosed needle holder it is merely necessary to detach the protective sleeve 28. The syringe is thus made ready since the needle 8 is already located in the correct working position. It will be appreciated that through the twisting of the hub part 24 with the base body 2 a stronger seating of the needle 8 is provided so that no additional outside help means is necessary and the entire arrangement is, without further, a workable single service syringe. For this purpose the protective sleeve 28 in known ways in the region of its free end 38 is smaller formed than the preparation holder 6 formed plunger and the preparation holder is provided in known ways ( not here disclosed ) with a plungerforming sliding plug in its other end.

FIG. 3 shows an embodiment in which a base body 302 is provided with a wide flange 305. This flange affords the advantage that the free rim of the protective sleeve 328 mounts in the tight screwed position, not on the metal cuff 318 but instead on the surface of flange 304 which is better suited for the sealing purpose. In this way can one in the tightly twisted condition obtain a seal 340 between the protective sleeve 328 and the base body 302.

FIG. 4 shows an embodiment in which the central passage 420 in the base body 402 narrows at the flange side end to a fitted seat for a corresponding tapered end piece 444 of the hub part 424. In this way a better sealing and a stronger seating of the needle can be obtained.

FIG. 5 illustrates an embodiment by which the base body 502 is attachable on a preparation holder 506. The contacting end of the preparation holder is closed in known ways with a closure 510 which is puncturable by the needle. The closure 510 is clamped between a flange 516 and a cuff 518. The attached base body 502 has a clearance 546 which corresponds to the dimensions of the accommodating end of the preparation holder 506 in which elastic points 548 are provided and which by the insertion of the preparation holder in the base body 502 engage behind the flange 516 and cuff 518. In the clearance 546 the base body seals with closing foil 550 puncturable by the needle (not shown in FIG. 5). With sterile storage of the needle holder such a seal is not ordinarily necessary. In general it will be appreciated to use the needle holder corresponding to the embodiment of FIGS. 1 and 2 for a stronger connection with the preparation holder.

FIG. 6 illustrates in schematic part representation an embodiment of a second threaded connection 630 which as a result of the elastic deformation of the protective sleeve 628 and the use of a saw tooth thread profile of the protective sleeve 628 is slipped on without rotation axial of the base body 602. As a result of the saw tooth form of the thread profile an axial pulling off of protective sleeve 528 is not possible. Also common, non saw tooth thread profiles can naturally be employed that the protective sleeve as a result of its elastic deformation allows axial pushing on whereby one has to employ, in each case, a correspondingly high axial force. In many cases therefore it will not be necessary to employ saw tooth thread profile; that is to say it is not ordinarily expected that the user of the needle holder will attempt to pull the protective sleeve off instead of twisting it.

With the embodiment shown in FIG. 6, a good seal between the protective sleeve 628 and the base body is contemplated similar to the embodiment of FIG. 3. With the pushing on of the protective sleeve 628 without threading there is available only a proportionately small contact pressure and here a separate seal 640 is provided in the form of a soft plastic material ring. Additionally the edge of the protective sleeve can taper or be provided with a circular rib about the inside of a proportionately large axial clearance a good seal to form.

FIG. 7 illustrates an embodiment in which an elastically flexible friction coupling is provided between the hub part 724 and the protective sleeve 728 in an axial direction. There exists in the disclosed embodiment a ring 752 of elastic flexible material mounted in a groove 754 of the hub part 724 and which has a light interference so that the ring is tightly seated in the protective sleeve 728. This friction coupling keeps the needle holder under axial bias on the base body with the initial assembly of the needle holder when the hub part 724 is inserted in the protective sleeve and the protective sleeve is threaded on the base body (not disclosed in FIG. 7). This insures that with the later resulting unthreading of the protective sleeve the first screw connection immediately makes engagement between the hub part and the base body and thereby provides that the hub part is screwed in the work position. It is appreciated that the friction coupling may be otherwise formed as, in particular, out of many rings.

FIG. 8 illustrates a embodiment in which the lower end of the needle is not sharpened but is provided with a stub terminating projection 856 of the hub part 824.

This embodiment is suitable for vials, for example eye-drop vials. In the embodiment shown in FIG. 8 an indication 858 is provided in the protective sleeve which points out to the user that he should loosen the protective sleeve by means of a rotating movement.

Other embodiments of the invention are possible without departing from its scope.

I claim:

1. A needle holder for medical syringes, in particular injection syringes and syringes for the removal of body fluids, and for vials and the like with a base body for the closure of the end of a preparation holder that presents a closure puncturable by a hollow needle, a hub part fastened to the hollow needle which is screwed by means of a first threaded connection with a base body to a work position in which an end of the needle punctures the closure of the preparation holder, a protective sleeve having an open end which is rotatably and detachably mounted on the base body and which surrounds the hub part and the therewith affixed hollow needle, and an axial gear tooth system provided between the hub part and the protective sleeve which connects and provides for common rotation of these parts while permitting relative axial movement between an initial threaded position of the hub part and the work position of the hub part; characterized in that between the body (2) and protective sleeve (28) a second threaded connection (30) is provided with a thread direction opposite the first threaded connection (22, 26) so that with the unthreading of the protective sleeve (28) from the base body (2) the hub part (24) which is drivingly connected to the protective sleeve (28) by the axial gear tooth system (32) is threaded to a work position.

2. The needle holder according to claim 1 characterized in that the second threaded connection (30) is dimensioned in such a manner that with the unscrewing of the protective sleeve (28) it becomes disengaged shortly before the work position of the hub part is reached.

3. The needle holder according to claim 2 characterized in that the axial gear tooth system (32) is so dimensioned that the rotating drive connection is undone after fully unscrewing and a further axial movement of the protective sleeve (28) in the removal direction.

4. The needle holder according to claim 1 characterized in that the second threaded connection (630) is provided with thread profiles which axially slide upon one another by the application of increased axial force. (FIG. 6)

5. The needle holder according to claim 4 characterized in that the second threaded connection (630) is provided with thread profiles which in the movement direction of protective sleeve (628) corresponding to screw tightening are slidable upon one another and in the movement direction of the protective sleeve (628) corresponding to unscrewing drive into one another.

6. The needle holder according to claim 1 characterized in that a friction coupling (752,754) elastically flexible in an axial direction is provided between the hub part (724) and the protective sleeve (728).

7. The needle holder according to claim 6 characterized in that the friction coupling exhibits at least one tightly seated ring (752) formed out of an elastically flexible material, such as plastic.

8. The needle holder according to claim 1 characterized in that the base body (2) is connected with a preparation holder (6). (FIG. 1)

9. The needle holder according to claim 1 characterized in that the base body (502) is assembled with a preparation holer (506). (FIG. 5)

10. The needle holder according to claim 9 characterized in that the base body (502) contains a sealing foil (550) puncturable with a needle on its end adjacent the preparation holer (506). (FIG. 5)

11. The needle holder according to claim 1 characterized as including an effective seal (340) between the protective sleeve (328) and the base body (302) with a tightly threaded on protective sleeve. (FIG. 3)

12. The needle holder according to claim 1 characterized in that the two threaded connections have differing thread pitches.

13. The needle holder according to claim 1 characterized in that the protective sleeve (828) is provided with a marking indicating the necessary rotation direction.

14. The needle holder according to claim 8 characterized in that it forms a part of a single use syringe.

15. A needle holder for medical syringes suitable for use with a container which presents a puncturable closure, said holder comprising:

a base body suitable for receiving the puncturable closure;

a hub part carrying an axially extending hollow needle, said hub part being mounted on said base body by a first threaded connection which, upon rotation of the hub part in a selected direction, provides axial movement of same towards said closure;

a protective sleeve surrounding the hub part and mounted on said base body by a second threaded connection oppositely threaded with respect to said first threaded connection; and a driving means coupling said protective sleeve to said hub part of transferring rotation of said protective sleeve to said hub part while permitting axial movement of said hub part with respect thereto, whereby the unthreading of the protective sleeve from the base body along said second threaded connection provides rotation of said hub part in the selected direction and causes axial movement of said hub part along said first threaded connection toward said puncturable closure.

* * * * *